US012611471B2

(12) United States Patent
Fan et al.

(10) Patent No.: US 12,611,471 B2
(45) Date of Patent: Apr. 28, 2026

(54) COMPOSITE FERRITE NANOPARTICLE WITH SYNERGISTIC ENHANCEMENT OF LIVER SPECIFICITY AND PREPARATION METHOD AND APPLICATION THEREOF

(71) Applicant: Xi'An SuperMag Bio-Nanotech Co., Ltd., Xi'An (CN)

(72) Inventors: Haiming Fan, Xi'An (CN); Huan Zhang, Xi'An (CN); Mingli Peng, Xi'An (CN); Xiaoli Liu, Xi'An (CN)

(73) Assignee: XI'AN SUPERMAG BIO-NANOTECH CO., LTD., Xi'an (CN)

( * ) Notice: Subject to any disclaimer, the term of this patent is extended or adjusted under 35 U.S.C. 154(b) by 585 days.

(21) Appl. No.: 18/005,349

(22) PCT Filed: Feb. 1, 2021

(86) PCT No.: PCT/CN2021/074662
§ 371 (c)(1),
(2) Date: Jan. 12, 2023

(87) PCT Pub. No.: WO2022/012029
PCT Pub. Date: Jan. 20, 2022

(65) Prior Publication Data
US 2024/0238455 A1 Jul. 18, 2024

(30) Foreign Application Priority Data
Jul. 14, 2020 (CN) .......................... 202010674899.0

(51) Int. Cl.
*A61K 49/18* (2006.01)
*B82Y 5/00* (2011.01)
*B82Y 25/00* (2011.01)
*B82Y 40/00* (2011.01)

(52) U.S. Cl.
CPC ........ *A61K 49/1833* (2013.01); *A61K 49/183* (2013.01); *B82Y 5/00* (2013.01); *B82Y 25/00* (2013.01); *B82Y 40/00* (2013.01)

(58) Field of Classification Search
None
See application file for complete search history.

(56) References Cited

FOREIGN PATENT DOCUMENTS

| | | |
|---|---|---|
| CN | 103153348 A | 6/2013 |
| CN | 110237272 A | 9/2019 |
| WO | 2009126835 A2 | 10/2009 |
| WO | 2011113616 | 9/2011 |

OTHER PUBLICATIONS

Zhang et al, (A dissertation submitted to Northwest University, Dec. 2018). (Year: 2018).*
Zhang, p. 20 (Year: 2018).*
Zhang, p. 24 (Year: 2018).*
Zhang, p. 77 (Year: 2018).*
Zhang, pp. 90-91 (Year: 2018).*

* cited by examiner

*Primary Examiner* — Celeste A Roney
(74) *Attorney, Agent, or Firm* — HOWARD M COHN and Associates, LLC

(57) ABSTRACT

A ferrite nano-composites with synergistic enhancement of liver specificity and preparation method and application thereof, wherein the ferrite nano-composites have both manganese ions and ethoxybenzyl group, and the molar percentage of ethoxybenzyl group to manganese ions is 25-60%. The molar percentages of manganese and ferric ions in the ferrite nanoparticles are 40-80%, and the ferrite nano-composites with manganese ions and ethoxybenzyl groups on the surface are in the particle size range of 0.2-5 nm, with preferred particle size range of 2-4 nm. With the preparation method and the application for magnetic resonance T1 imaging, the ferrite nano-composites enhance hepatocyte specificity due to the synergistic effect of manganese ions and ethoxybenzyl groups, thus achieving enhanced T1 imaging of the liver with high specificity in magnetic resonance imaging.

8 Claims, 4 Drawing Sheets

COMPOSITE FERRITE NANOPARTICLE WITH SYNERGISTIC ENHANCEMENT OF LIVER SPECIFICITY AND PREPARATION METHOD AND APPLICATION THEREOF

1. TECHNICAL FIELD

The invention relates to the field of material science and biomedical technology, in particular to a composite ferrite nanoparticle with synergistic enhancement of liver specificity and preparation method and application thereof.

2. BACKGROUND ART

Among the available report for the liver-specific contrast agents, there are superparamagnetic iron oxide nanoparticles T2 contrast agents targeting liver macrophages. However, the intrinsic low signal of T2 imaging is easily confused with the low signal of hemorrhage, calcification and metal deposits in biological tissues, and T2 imaging itself is prone to artifacts and poor contrast. When adopting gadolinium based T1 contrast agent targeted to hepatocytes, the ethoxybenzyl group can specifically identify hepatocytes and achieve liver-specific imaging. However, gadolinium-based contrast agents are cleared through the kidneys, which can easily cause systemic renal fibrosis or even renal failure, and gadolinium ions are easily dissociated in the body and remain in the central nervous system for a long time, posing a potential risk to the human body. Most importantly, the targeting efficiency of gadolinium-based contrast agents in the liver is merely less than 50%, limiting highly sensitive imaging of the liver.

In recent years, there have been great advances in ultra-small magnetic nanoparticles, such as the first report of 4.9 nm $\gamma$-Fe2O3 as a T1 contrast agent by Robert N. Muller's team in 2007 (Langmuir, 2007, 23(8): 4583-4588). Horst Weller et al. reported that the size of iron oxide nanoparticles that can be used as T1 contrast agents should be less than the threshold of 5 nm and investigated the effect of iron oxide modification on the stability, relaxation rate, cytotoxicity and phagocytosis of macrophages on the surface of polyethylene glycol (PEG) of different chain lengths (Nano Letters, 2009, 9(12): 4434-4440). Taeghwan Hyeon's research team adopted ferric oleate as a precursor to prepare extremely small size $\gamma$-Fe2O3 nanoparticles (1.5 nm-3.7 nm) on a large scale and evaluated its in vivo vascular imaging effect using 3 nm iron oxide nanoparticles as a model system (J. Am. Chem. Soc., 2011, 133(32):12624-12631). In Chinese invention patent CN 103153348 B, Lu Gaoqing (Adv. Funct. Mater. 2012, 22, 2387-2393), Gao Mingyuan (Adv. Funct. Mater. 2012, 22, 2387-2393) and others also reported the synthesis of ultra-small ferrous oxides particle and optimize the T1 relaxation performance by surface modification with polymers such as PEG, respectively. The Moungi G. Bawendi research team also developed novel infinitesimally small size of superparamagnetic iron oxide nanoparticles for T1 contrast agents (Proc. Nat. Acad. Sci., 2017, 114(9): 2325-2330.). The above study shows that the preparation of ultra-small magnetic nanoparticles is of great clinical and scientific significance for their application as T1 contrast agents for magnetic resonance imaging.

3. SUMMARY OF THE INVENTION

To address the current issues of detection accuracy and safety faced by liver contrast agents, the invention adopts ultra-small ferrite nanoparticles and ethoxybenzyl group structure to achieve highly specific hepatocyte-targeted imaging by using ferrite nanoparticles as MRI liver-specific T1 contrast agents. Meanwhile, the synergistic effect of manganese ions and ethoxybenzyl groups of the nanoparticle can increase the specificity of hepatocytes, to achieve uniform strengthening of the liver and improve the detection accuracy, and realize the final rapid clearance through the hepatobiliary system.

To achieve the above functions, the invention provides the following technical solutions: a composite ferrite nanoparticle with synergistic enhancement of liver specificity, wherein the ferrite nano-composites have both manganese ions and ethoxybenzyl group, and the molar percentage of ethoxyphenyl group and manganese ions is 25-60%, and the ethoxyphenyl group is a polyethylene glycol modified with ethoxybenzyl at one end, and the other end of the polyethylene glycol modified with one of carboxy, amines, dopamine, diphenol, hydroxy group and phospholipid, and the molecular weight of the polyethylene glycol with ethoxybenzyl group is 800-20,000.

Further, the molar percentage of manganese and ferric ions in the ferrite nanoparticles described is 40-80%, and the particle size of the composite ferrite nanoparticles with manganese ions and ethoxybenzyl groups on the surface is 0.2-5 nm.

Further, the particles size of the ferrite nano-composites with manganese ions and ethoxybenzyl groups on the surface is 2-4 nm.

The invention also provided the preparation method for a ferrite nano-composites with synergistic enhancement of liver specificity, comprising the following steps:

S1. dissolving the polyethylene glycol modified by ethoxybenzyl group and the ferrite nanoparticles containing manganese in a mixed solvent to form a homogeneous reaction system.

S2. heating the reaction system in S1 to 30-80° C. in an inert gas atmosphere, and after finishing the reaction for 2-8 h, washing and precipitating with polar solvents, and obtaining a kind of ferrite nano-composites containing manganese ions on the surface after centrifugation.

Further, the manganese ions on the surface of the ferrite nanoparticles can be prepared by doping during preparation or by exchanging metal ions on the surface.

Further, the mixed solvents in S1 are: one or more mixed solvent systems of tetrahydrofuran, ethyl acetate, acetonitrile, water, diethyl ether, dimethyl sulfoxide and dimethyl formamide polar solvents; the moderate polar solvents in S2 are one or more mixed solvent systems of tetrahydrofuran, ethyl acetate, acetonitrile, water, diethyl ether, dimethyl sulfoxide and dimethyl formamide polar solvents.

The invention also provides the application for a ferrite nano-composites with synergistic enhancement of liver specificity, wherein the aqueous solution of ferrite nano-composites with manganese ions and ethoxybenzyl groups on the surface can be applied for enhanced MRI T1 imaging of the liver with high specificity.

Further, the concentration of the composite ferrite nanoparticles aqueous solution is 0.1-10 mg/ml and the application dose is 0.3-1000 mg/kg.

Compared to the prior arts, the invention has the following beneficial effects: a ferrite nano-composites with synergistic enhancement of liver specificity provided by the invention is an ultra-small ferrite nanoparticle made by combining the specificity of manganese ions and ethoxybenzyl, which can significantly improve hepatocyte targeting when used as a magnetic resonance T1 contrast agent.

The preparation method for a ferrite nano-composites with synergistic enhancement of liver specificity provided by the invention can achieve the control of the ratio of ethoxybenzyl groups to manganese ions by controlling the concentration of reactants, reaction time and reaction temperature, thus optimizing the synergistic effect of targeting hepatocytes. The application for a ferrite nano-composites with synergistic enhancement of liver specificity provided by the invention can achieve uniform enhancement of liver T1 imaging through the concentration and dosage of contrast agent for making hepatocytes from ferrite nano-composites, thus guaranteeing the accuracy and safety of liver imaging.

4. BRIEF DESCRIPTION OF ACCOMPANY DRAWINGS

5. SPECIFIC EMBODIMENT OF THE INVENTION

Figure 1:
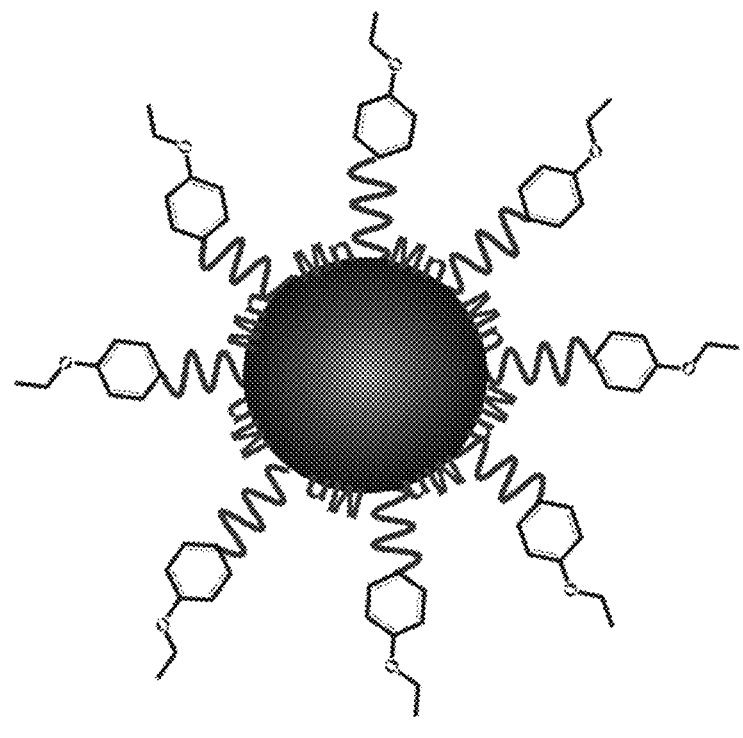
FIG. 1 is a schematic diagram showing the structure of the ultra-small ferrite nano-composites with manganese ions and ethoxybenzyl groups on the surface of the invention.

To make the technical solutions provided by the unity model more comprehensible, exemplary embodiments according to the application are described below in detail with reference to the accompanying drawings. Apparently, the described embodiments are merely some embodiments of the application rather than all the embodiments of the application. It should be understood that the application is not limited to the exemplary embodiments described herein. Based on the embodiments in the invention, all other embodiments obtained by those of ordinary skill in the art without making creative labor shall fall within the scope of protection of the invention.

Embodiment 1

The preparation method for the ferrite nano-composites with synergistic enhancement of liver specificity of the invention is as follows: dispersing 20 mg of manganese ferrite nanoparticles and 80 mg of dopamine-polyethylene glycol (Mw=1000)-ethoxybenzene molecules in 12 ml of tetrahydrofuran solution and stirring well under argon atmosphere to obtain a homogeneous mixture, in which the molar ratio of manganese to ferrum is 0.52; heating the mixture to 50° C. and keeping it for 5 h for the reaction, and cooling the mixture naturally to room temperature after the reaction;

taking 10 mL of diethyl ether and adding it to the mixture, stirring to appear precipitation, and then carrying out centrifugation to separate; dissolving the product obtained by centrifugal separation in deionized water to obtain composite ferrite nanoparticles containing manganese ions and ethoxybenzyl groups, with the result analysis showing that the molar percentage of ethoxybenzyl to manganese ions was 46%.

Embodiment 2

The preparation method for the ferrite nano-composites with synergistic enhancement of liver specificity of the invention is as follows: dispersing 20 mg of manganese ferrite nanoparticles and 50 mg of 3-(4-Ethoxyphenyl)propionic acid in 10 ml of tetrahydrofuran solution and stirring well under argon atmosphere to obtain a homogeneous mixture, in which the molar ratio of manganese to ferrum is 0.61; heating the mixture to 60° C. and keeping it for 4 h for the reaction, and cooling the mixture naturally to room temperature after the reaction; taking 10 mL of diethyl ether and adding it to the mixture, stirring to appear precipitation, and then carrying out centrifugation to separate; dissolving the product obtained by centrifugal separation in deionized water to obtain ferrite nano-composites containing manganese ions and ethoxybenzyl groups, with the result analysis showing that the molar percentage of ethoxybenzyl to manganese ions was 39%.

Embodiment 3

The preparation method for the ferrite nano-composites with synergistic enhancement of liver specificity of the invention is as follows: dispersing 20 mg of manganese ferrite nanoparticles and 120 mg of dopamine-dextran (Mw=2000)-ethoxybenzene molecules in 12 ml of tetrahydrofuran solution and stirring well under argon atmosphere to obtain a homogeneous mixture, in which the molar ratio of manganese to ferrum is 0.52; heating the mixture to 60° C. and keeping it for 5 h for the reaction, and cooling the mixture naturally to room temperature after the reaction; taking 10 mL of acetone and adding it to the mixture, stirring to appear precipitation, and then carrying out centrifugation to separate; dissolving the product obtained by centrifugal separation in deionized water to obtain ferrite nano-composites containing manganese ions and ethoxybenzyl groups, with the result analysis showing that the molar percentage of ethoxybenzyl to manganese ions was 28%.

Figure 2:
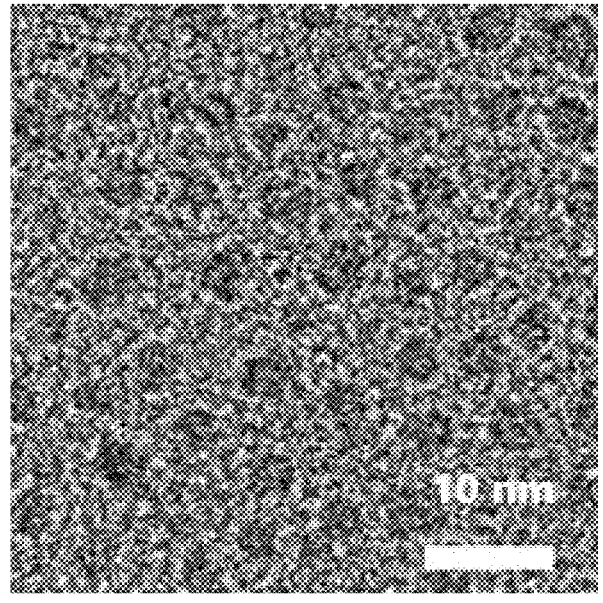
FIG. 2 is a schematic diagram showing the TEM of the ultra-small ferrite nano-composites of embodiment 1 of the invention.
Figure 3:
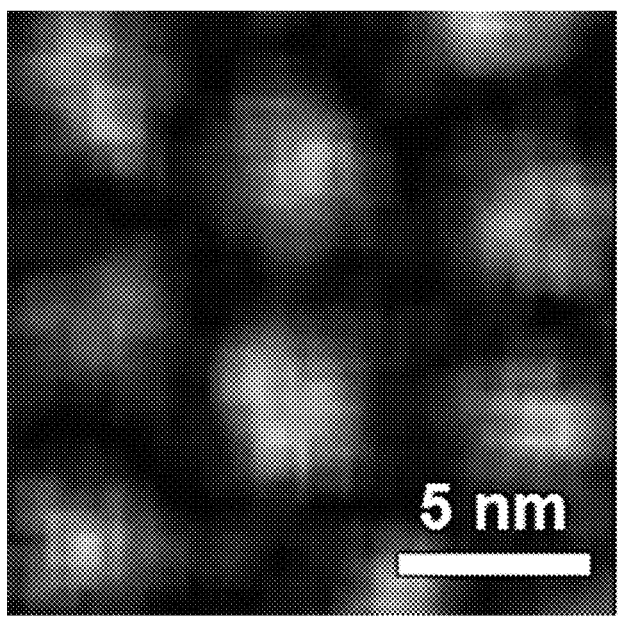
FIG. 3 is a schematic diagram showing the distribution of manganese elements in the ultra-small ferrite nano-composites of embodiment 1 of the invention.
Figure 4:
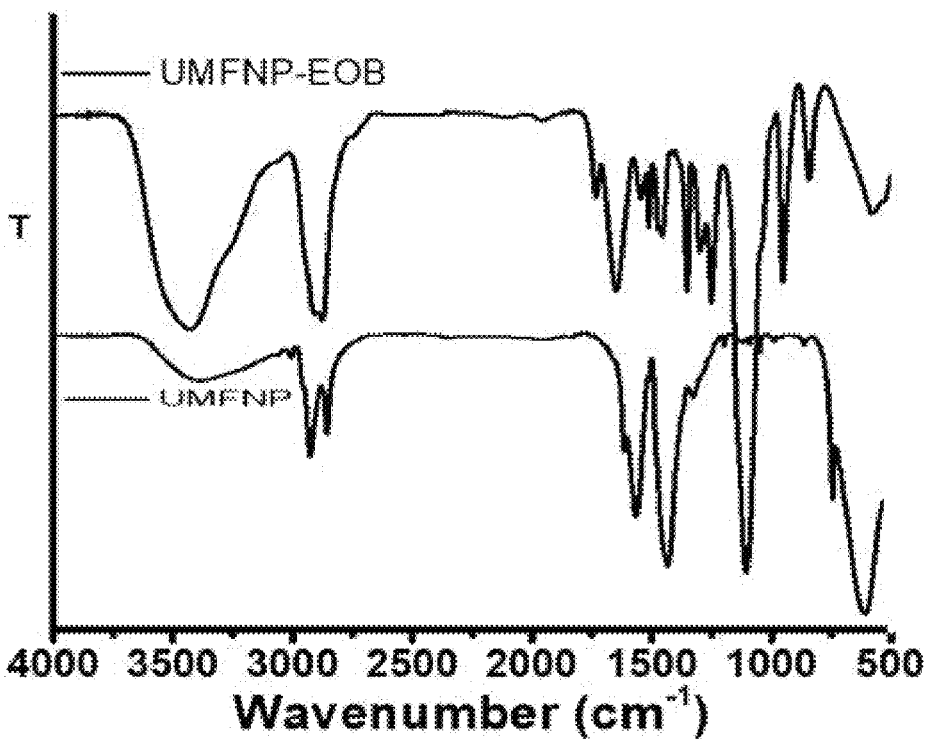
FIG. 4 is a schematic diagram showing the Infrared spectrum of the ultra-small ferrite nano-composites of embodiment 1 of the invention.
Figure 5:
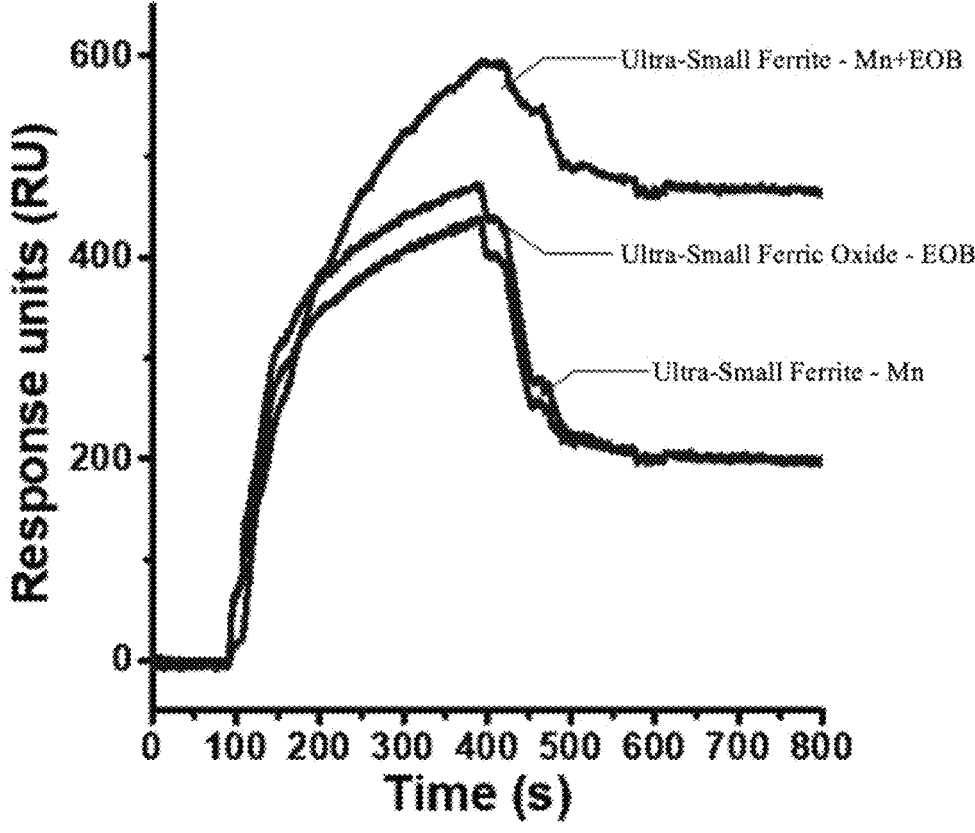
FIG. 5 is a schematic diagram showing an analysis of the Surface Plasmon Resonance (SPR) detection results of hepatocytes by ultra-small ferrite nano-composites with manganese ions and ethoxybenzyl groups on the surface of embodiment 1 of the invention.
Figure 6:
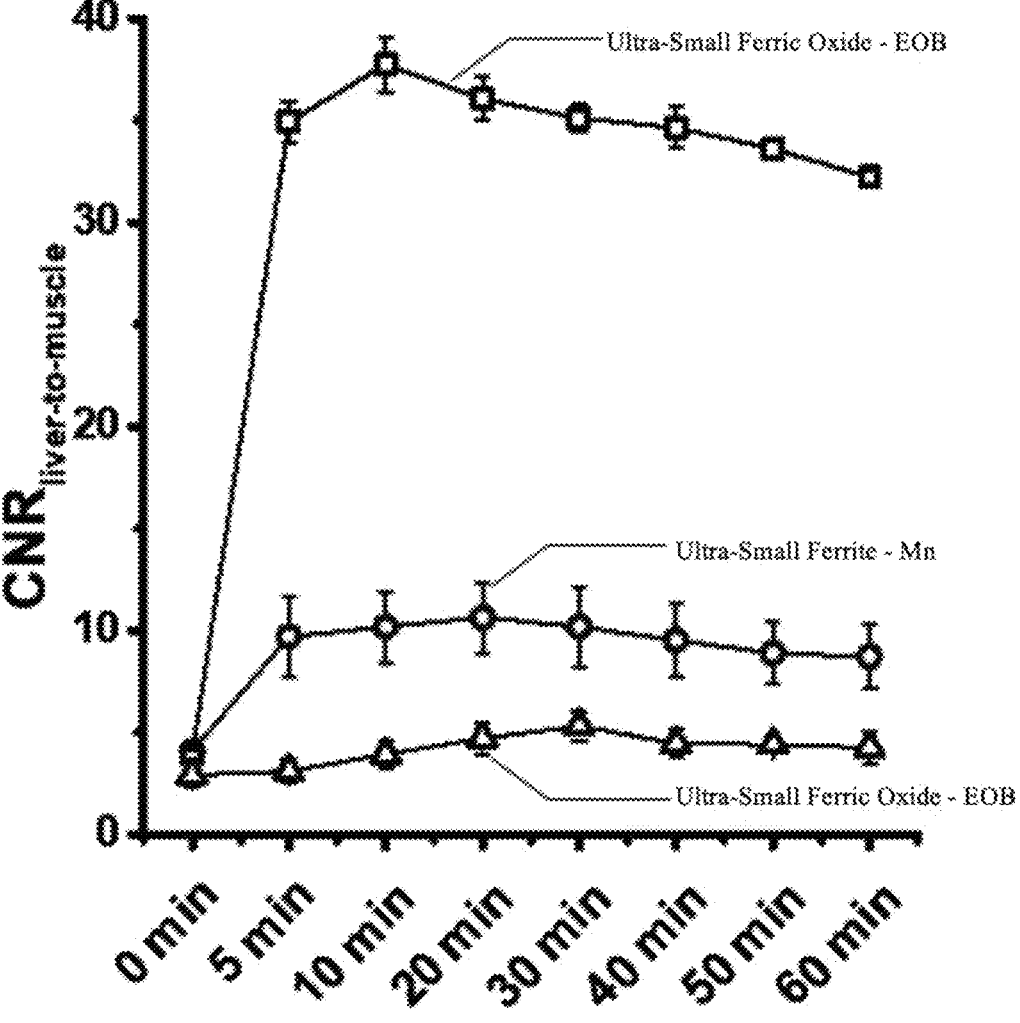
FIG. 6 is a schematic diagram showing a graphical analysis of the contrast variation of liver MRI with ultra-small ferrite nano-composites with manganese ions and ethoxybenzyl groups on the surface of embodiment 1 of the invention.

The ferrite nano-composites prepared in Embodiment 1 were characterized by dispersing the composite ferrite nanoparticles containing manganese ions and ethoxybenzyl groups in n-hexane, taking 2 μL of the n-hexane solution with the nanoparticles dispersed on a copper network coated with a carbon film, and then characterizing them after natural drying. FIG. 1 is a schematic diagram showing the structure of the ultra-small ferrite nano-composites with manganese ions and ethoxybenzyl groups on the surface of the invention, and FIG. 2 is a TEM schematic diagram. Referring to the FIG. 2, the ultra-small ferrite nano-composites containing manganese ions and ethoxybenzyl groups are homogeneous in size and shape, with monodispersed and size around 3 nm. FIG. 3 is a schematic diagram showing the distribution of manganese elements. Referring to the FIG. 3, the manganese is uniformly distributed in the particles, indicating that the nanoparticles contain manganese and the ratio of manganese to ferrum is 0.52 from the results of the AES-ICP. FIG. 4 is a schematic diagram showing the Infrared spectrum. Referring to the FIG. 4, it can be seen that there are significant characteristic absorption peaks of ethoxybenzyl around 1100, 1400-1500, indicating that ethoxybenzyl is attached to the ferrite nano-composites. FIG. 5 shows the binding strength of different nanoparticles modified on the surface of gold chip to hepatocytes by Surface Plasmon Resonance (SPR). Referring to the FIG. 5, it can be seen that the nanoparticles containing manganese ions and ethoxybenzyl groups have the strongest binding strength to hepatocytes, which achieves the highest specificity to hepatocytes, and manganese ions and ethoxybenzyl groups have a synergistic effect, which is significantly stronger than the specificity of nanoparticles containing single manganese ions and single ethoxybenzyl groups. FIG. 6 is a schematic diagram showing a graphical analysis of the contrast variation of liver MRI with composite ultra-small ferrite nano-composites with manganese ions and ethoxybenzyl groups on the surface, wherein the contrast is calculated by measuring liver tissue MRI signal, muscle tissue MRI signal and noise signal, and the calculation formula is: liver-muscle contrast=(liver T1 signal intensity−muscle T1 signal intensity)/noise signal intensity. It can be seen that nanoparticles containing manganese ions and ethoxybenzyl groups have the best contrast enhancement of hepatocytes in the liver, with the liver-muscle contrast being 10 times higher than that of the other particles, further indicating that nanoparticles containing manganese ions and ethoxybenzyl groups contribute to their specificity for hepatocytes due to the synergistic effect of manganese ions and ethoxybenzyl groups. The above results show that nanoparticles containing manganese ions and ethoxybenzyl groups on the surface can synergistically potentiate hepatocyte specificity.

The invention and the embodiments thereof are described hereinabove, and this description is not restrictive. What is shown in the drawings is only one of the embodiments of the invention, and the actual structure is not limited thereto. In summary, structural methods and embodiments similar to the technical solution without departing from the inventive purpose of the invention made by inspired ordinary technicians in the art without creative efforts shall all fall within the protection scope of the invention.

The invention claimed is:

1. A ferrite nano-composite with synergistic enhancement of liver specificity, wherein the ferrite nano-composite has both manganese ions and ethoxybenzyl group, and the molar percentage of ethoxybenzyl group and manganese ions is 25-60%, and the ethoxybenzyl group is a polyethylene glycol modified with ethoxybenzyl at one end, and the other end of the polyethylene glycol modified with one of carboxy, amines, dopamine, diphenol, hydroxy group and phospholipid, and the molecular weight of the polyethylene glycol with ethoxybenzyl group is 800-20,000.

2. A ferrite nano-composite with synergistic enhancement of liver specificity according to claim 1, wherein the molar percentage of manganese and ferric ions in the ferrite nano-composite is 40-80%, and the particle size of the ferrite nano-composite with manganese ions and ethoxybenzyl groups on a surface of the ferrite nano-composite is 0.2-5 nm.

3. A ferrite nano-composite with synergistic enhancement of liver specificity according to claim 2, wherein the particles size of the ferrite nano-composite with manganese ions and ethoxybenzyl groups on the surface is 2-4 nm.

4. A ferrite nano-composite with synergistic enhancement of liver specificity and preparation method thereof according to any claim 1 to claim 3, wherein the method comprises the following steps:

S1. dissolving the polyethylene glycol modified by ethoxybenzyl group and ferrite nanoparticles containing manganese ions in a mixed solvent to form a homogeneous reaction system;

S2. heating the reaction system in S1 to 30-80° C. in an inert gas atmosphere, and after finishing the reaction for 2-8 h, washing and precipitating with polar solvents, and obtaining a kind of ferrite nano-composite containing manganese ions and ethoxybenzyl group on a surface of the ferrite nano-composite after centrifugation.

5. A ferrite nano-composite with synergistic enhancement of liver specificity and preparation method thereof according to claim 4, wherein the manganese ions on the surface of the ferrite nanoparticles can be are prepared by doping during preparation or by exchanging metal ions on the surface.

6. A ferrite nano-composite with synergistic enhancement of liver specificity and preparation method thereof according to claim 4, wherein the mixed solvent in S1 is: one or more mixed solvent systems of tetrahydrofuran, ethyl acetate, acetonitrile, water, diethyl ether, dimethyl sulfoxide and dimethyl formamide polar solvents; the polar solvents in S2 are one or more mixed solvent systems of tetrahydrofuran, ethyl acetate, acetonitrile, water, diethyl ether, dimethyl sulfoxide and dimethyl formamide polar solvents.

7. A ferrite nano-composite with synergistic enhancement of liver specificity and application thereof according to any claim 1 to claim 3, wherein an aqueous solution of the ferrite nano-composite is applied for enhanced MRI T1 imaging of the liver with high specificity.

8. A ferrite nano-composite with synergistic enhancement of liver specificity and application thereof according to claim 7, wherein the concentration of the aqueous solution of the ferrite nano-composite is 0.1-10 mg/ml and the application dose is 0.3-1000 mg/kg.

\* \* \* \* \*